US005543401A

United States Patent [19]
Stolfi

[11] Patent Number: 5,543,401
[45] Date of Patent: Aug. 6, 1996

[54] UDPG AS A RESCUE AGENT IN CANCER THERAPY AFTER THE ADMINISTRATION OF ANTIPYRIMIDINE OR RELATED ANTI-TUMOR AGENTS WITH OR WITHOUT BAU

[75] Inventor: Robert L. Stolfi, Harrison, N.Y.

[73] Assignee: Boehringer Mannheim Italia SpA, Monza, Italy

[21] Appl. No.: 354,861

[22] Filed: Dec. 9, 1994

Related U.S. Application Data

[62] Division of Ser. No. 178,360, Jan. 6, 1994, which is a continuation of Ser. No. 599,927, Oct. 19, 1990, abandoned.

[51] Int. Cl.$^6$ .................... A61K 31/70; A61K 31/695; A61K 31/505
[52] U.S. Cl. .................. 514/50; 514/51; 514/63; 514/274
[58] Field of Search ................ 514/50, 51, 63, 514/274

[56] References Cited

U.S. PATENT DOCUMENTS 4,868,189  9/1989  Kurono et al. .................... 514/274

FOREIGN PATENT DOCUMENTS

WO86/03678  7/1986  WIPO .

OTHER PUBLICATIONS

Colofiore et al., Pharmaceutical Research Official Journal of the American Association of Pharmaceutical Scientists, vol. 6, No. 10, pp. 863–866, Oct. 1989.

Yip et al., Biochemical Pharmacology, vol. 36, No. 5, pp. 633–637, Mar. 1, 1987

Martin et al, "Use of Oral Uridine as a Substitute for Parenteral Uridine Rescue of 5–Fluorouracil Therapy, With and Without the Uridine Phosphorylase Inhibitor 5–Benzylacyclouridine", *Cancer Chemotherapy and Pharmacology*, 24, 1989, pp. 9–14.

Darnowski et al, "Tissue–specific Enhancement of Uridine Utilization and 5–Fluorouracil Therapy in Mice by Benzylacyclouridine", *Cancer Research*, vol. 45, Nov. 1985, pp. 5364–5368.

Groeningen et al, "Clinical and Pharmacokinetic Studies of Prolonged Administration of High–Dose Uridine Intended for Resue From 5–FU Toxicity", *Cancer Treatment Reports*, vol. 70, No. 6, Jun. 1986, pp. 745–750.

Groeningen et al, "Reversal of 5–Fluorouracil Induced Myelosuppression by Prolonged Administration of High–Dose Uridine", *Reports*, Journal of the National Cancer Institute, vol. 81, No. 2, Jan. 18, 1989, p. 157.

Colofiore et al, "Effect of Uridine Diphosphoglucose on Levels of 5–Phosphoribosyl Pyrophosphate and Uridine Triphosphate in Murine Tissues", *Pharmaceutical Research*, vol. 6, No. 10, 1989, pp. 863–866.

*Primary Examiner*—John W. Rollins
*Attorney, Agent, or Firm*—Nikaido, Marmelstein, Murray & Oram LLP

[57] ABSTRACT

A method of rescuing healthy cells of a cancer patient being treated with antipyrimidine antitumor compounds, or related compounds. Rescue is accomplished by administering UDPG after administering the antipyrimidine antitumor compound preferably with BAU administration.

24 Claims, 2 Drawing Sheets

UDPG AS A RESCUE AGENT IN CANCER THERAPY AFTER THE ADMINISTRATION OF ANTIPYRIMIDINE OR RELATED ANTI-TUMOR AGENTS WITH OR WITHOUT BAU

This is a division of application Ser. No. 08/178,360, filed Jan. 6, 1994, which is a continuation of Ser. No. 07/599,927, filed Oct. 19, 1990, now abandoned.

FIELD OF THE INVENTION

The present invention relates to the oral and intravenous administration of Uridine Diphosphoglucose (UDPG) as a rescue agent in cancer therapy after the administration of pyrimidine inhibitors or antipyrimidine compounds known as anti-tumor compounds and related compounds exhibiting similar activity with or without the administration of 5-benzylacyclouridine.

BACKGROUND OF THE INVENTION

In the field of anti-cancer chemotherapy it has been known for more than 25 years that solid tumors are amenable to treatment with antipyrimidine drugs i.e., pyrimidine inhibitors, such as 5-fluorouracil (5-FU or FU). (Darnowski et al, "Tissue-specific Enhancement of Uridine Utilization and 5-fluorouracil Therapy in Mice by Benzylacyclouridine", *Cancer Research* Vol 45, November 1985, pg. 5364). As discussed in The Pharmacological Basis of Therapeutics (Goodman & Gilman 5th Ed. 1975) pgs. 1272–1277 the therapeutic effect of 5-FU does not exist with the drug per se but in its enzymatically produced metabolite 5-fluoro-2'-deoxyuridine- 5'-phosphate (F-dUMP) a nucleotide. This nucleotide has an unusually great affinity for the enzyme thymidylate synthetase resulting in a decreased DNA synthesis. A second mechanism of action of 5-FU may involve the incorporation of 5-fluoro-uridine- 5'-triphosphate into RNA leading to impaired processing of nuclear RNA. (Groeningen et al, "Reversal of 5-fluorouracil Induced Myelosuppression by Prolonged Administration of High-Dose Uridine", *Reports,* Journal of the National Cancer Institute, Vol. 81, No. 2, Jan. 18, 1989, pg. 157). It has also been shown that 5-fluoro- 2'-deoxyuridine-5'-triphosphate (FdUTP) is incorporated in DNA.

5-FU and other related antipyrimidine chemicals used alone or in combination with other anticancer agents are toxic to cancer cells and normal healthy cells. Accordingly, the dose of antipyrimidine compounds administered to patients undergoing cancer therapy is limited by the toxic effects exhibited by such compounds. It is also noted that the therapeutic index of such compounds, in general, is low. The low therapeutic index and the toxicity associated with such drugs has provided motivation for increasing the anti-tumor activity of the antipyrimidine drugs and decreasing toxic effects to host tissue. Positive results with 5-FU have been achieved by combining this antipyrimidine with other anti-cancer agents, such as methotrexate and N-(phosphonacetyl)-L-aspartate, PALA. It has also been demonstrated that healthy tissue, subjected to the toxic effects of certain antipyrimidine anti-cancer agents, can be selectively rescued by the subsequent administration of large doses of uridine which results in the elevation of plasma uridine concentrations in the plasma such that millimolar or high micromolar uridine levels can be measured in the plasma drawn from a patient (Darnowski et al Id.). The administration of uridine increases the pool of uridine available to both healthy and diseased cells and thus accelerates the clearance of the anti-cancer agent from these cells as the uridine competes with the anti-cancer agent. However, the normal cells are reported to clear the anti-tumor agent quicker than the cancer cells by selectively taking up uridine. Thus, uridine administration has been shown to provide rescue, resulting in an increased therapeutic effect, after the administration of antipyrimidine anti-cancer agents.

However, rescue with uridine is not without risk of debilitating side effects. It is reported that when uridine is taken intravenously patients experience fever and phlebitis (Martin et al, "Use of Oral Uridine as a Substitute for Parenteral Uridine Rescue of 5-fluorouracil Therapy, With and Without the Uridine Phosphorylase Inhibitor 5-benzylacyclouridine", *Cancer Chemother Pharmacol,* 24, 1989, pgs. 9–14). Phlebitis can be avoided. However, this requires administering uridine orally or through a central vein. Using the central vein as a route of administration is complicated and has inherent risks, but even central vein administration does not eliminate the incidence of fever. Intermittent administration of uridine is effective in preventing or lowering the incidence of fever but fever still develops in some patients, and all of these patients still suffer the risk and disadvantages of central vein administration.

To overcome these disadvantages it has been proposed to administer uridine orally. However, in order to rescue healthy cells and tissue, large doses of uridine are required. Uridine in large doses irritates the gastrointestinal tract, which frequently causes severe diarrhea. In cancer patients such a condition not only lowers the quality of the patient's life but subjects the less-than-healthy patient to the loss of fluids and electrolytes necessary for kidney maintenance. Of course, antipyrimidine chemotherapy may be only one of a number of treatments being simultaneously administered to the patient, and, therefore, any loss of fluid level caused by severe diarrhea may be fatal to the patient. Accordingly, the oral administered dose of uridine is limited by its toxicity and the limited dose may not provide successful rescue.

In order to be effective the administered uridine must be retained by the body long enough to allow for the incorporation of uridine into cells. However, at the liver level uridine is quickly catabolized and the breakdown compounds are easily, excreted from the body. The use of 5-benzylacyclouridine (BAU), a phosphorylase inhibitor, in combination with uridine rescue is known to enhance the rescue effect by preventing the premature catabolism of uridine. The use of BAU prevents the breakdown of uridine by phosphorylase and the subsequent rapid body clearance of uridine, and thus slows the rate of uridine catabolism (Martin et al Id.). However, the administration of BAU fails to cure or eliminate all of the problems associated with administering i.v. uridine to patients.

SUMMARY OF THE INVENTION

The present invention relates to the oral administration of UDPG, which provides uridine plasma concentrations necessary to produce a rescue effect, and which appears to prevent diarrhea associated with the oral administration of rescue effective amounts of uridine. Therefore, UDPG can be administered without surgical intervention and without the risks associated with oral administration of uridine. As a result of this finding it is now possible to safely increase uridine levels in plasma by administering UDPG after administering one or more antipyrimidine anticancer drugs or after administering antipyrimidine anticancer drugs in combination with other types of anticancer drugs. Because non-toxic rescue is now possible the dosage of an antipyrimidine anti-cancer agent can be increased. Thereafter, the therapeutic effect of the antipyrimidine anti-cancer agent is increased and/or the toxicity of the pyrimidine anti-cancer agent to healthy cells is simultaneously lowered.

Accordingly, the present invention relates to a method of rescuing the healthy cells of a cancer patient being treated with antipyrimidine anti-tumor compounds. Rescue is accomplished by administering rescue effective amounts of UDPG to the patient after the administration of the anti-tumor agent.

The invention also relates to orally administering rescue effective amounts of UDPG to cancer patients.

The invention also relates to UDPG rescue in association with BAU administration after the administration of antipyrimidine anticancer drugs or after the administration of antipyrimidine anticancer drugs in combination with other anticancer drugs.

The invention also relates to a pharmaceutical kit composed of at least anticancer effective amounts of an antipyrimidine or pyrimidine inhibitor and rescue effective amounts of UDPG.

DETAILED DESCRIPTION OF THE INVENTION

Figure 1:
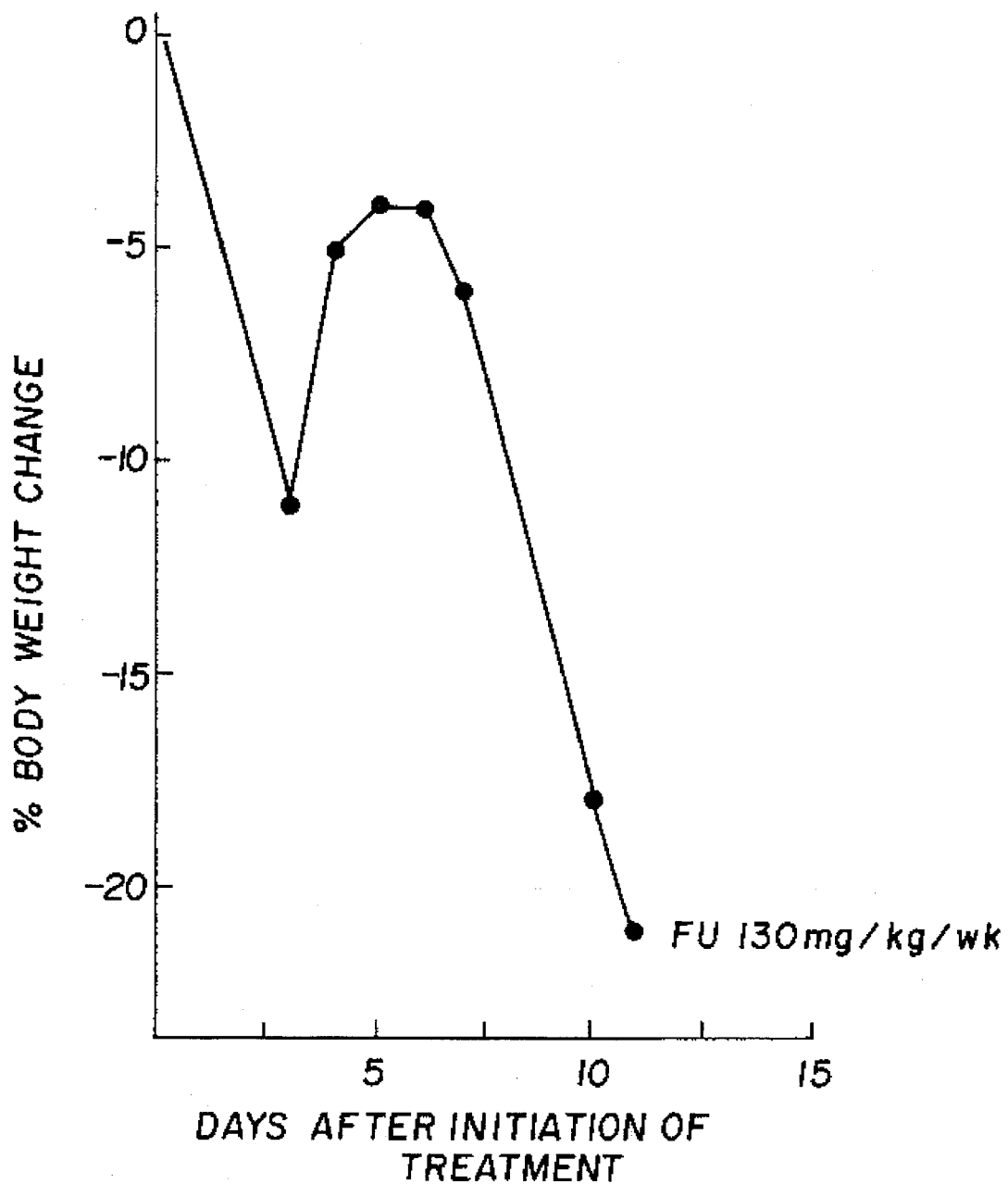
FIG. 1 is a plot showing the toxicity of 5-fluorouracil. Toxicity in the plot is measured as a function of the percent of body weight change over time. The plot shows the change in body weight of mice after the administration of 5-fluorouracil.

The present invention relates to the use of UDPG as an agent for the rescue of healthy cells after the administration of an effective dose of an antipyrimidine anti-cancer drug used in the chemotherapy of a cancer patient. The present invention uses UDPG as a source of uridine, which is preferentially taken up by healthy cells and, therefore, functions as a rescue agent in antipyrimidine anticancer chemotherapy.

The anti-cancer agents which can be used in association with rescue by UDPG include antipyrimidine type anti-cancer compounds including 5-fluorouracil (5-FU or FU), 5-fluorouracil derivatives such as the organo-silicone compounds disclosed in U.S. Pat. No. 4,868,189, incorporated by reference herein, 1-(2-tetrahydrofuryl)- 5-fluorouracil, and 1-[2-[(2-dimethyl-n-octyl-silyl-5-ethyl)thio]ethylcarbamoyl-5-fluoro-uracil disclosed in European Patent Application 186,452 Tegafur, Carmofur, cytosine arabinoside and other antipyrimidine anti-tumor agents may also be used. Of course, metabolic precursors of 5-FU (or of F-dUMP) can be utilized. The list above is not exhaustive but merely provides a reference to examples. The list is not intended to limit the invention in any way.

The types of tumors to be treated by the method of the invention, especially in humans, include tumors of the gastrointestinal tract (esophagus, stomach, colon, rectum), breast, prostate, ovaries, liver, head and neck and pancreas.

5-FU and other related antipyrimidine compounds are administered to human cancer patients according to different schedules, as is well known to those with ordinary skill in the art. For example, in one schedule an antipyrimidine compound is only administered during the first five days of a monthly schedule. In a second schedule the antipyrimidine compound is administered once a week. In a third schedule, the antipyrimidine compound is given by a continuous infusion every hour of the day for months. This last schedule is made possible by low dose administration with miniature pumps.

A representative schedule of clinical administration includes administering weekly i.v. injections of a bolus of 5-FU on an outpatient basis. A typical starting dose is about 500 mg/m$^2$. Every four weeks the 5-FU dose is increased by 20% until dose-limiting toxicity occurs, which can be indicated by weight loss, or destruction of bone marrow cells and the loss of white blood cells. Table 1 shows the toxic dose of weekly 5-FU administrations and severity of myelosuppression.

TABLE 1

Toxic dose of weekly 5-FU and severity of myelosuppression

| Patient No. | Age (yr.) | Sex | Performance Status (WHO) | Prior chemo-therapy* | Toxic dose (mg/m$^2$) | Nadir at toxicity wbc (×10$^6$/mL) | Platelets (×10$^6$/mL) |
|---|---|---|---|---|---|---|---|
| 1 | 57 | F | 1 | None | 720 | 1.6 | 151 |
| 2 | 70 | F | 1 | None | 600 | 2.7 | 101 |
| 3 | 66 | F | 0 | HAI 5-FU | 600 | 1.4 | 76 |
| 4 | 62 | M | 2 | None | 864 | 2.8 | 110 |
| 5 | 61 | F | 1 | None | 864 | 2.0 | 205 |
| 6 | 55 | M | 1 | HAI 5-FU | 864 | 4.3 | 84 |
| 7 | 74 | M | 1 | TGU | 600 | 6.7 | 82 |
| 8 | 55 | M | 1 | None | 720 | 4.1 | 95 |
| 8 | 49 | F | 0 | FAC | 720 | 3.7 | 74 |

*HAI = hepatic arterial infusion, TGU = 1,2,4-triglycidylurazol, FAC = 5-fluorouracil-doxorubicin-cyclophosphamide.

Conventionally, in the weekly schedule discussed above, on the onset of toxicity, the administration of 5-FU is followed in three hours by the administration of uridine. For example, after the administration of 5-FU, uridine is administered three hours later by intermittent i.v., in a central venous infusion. Three hour infusions of uridine are made to provide a dose of 2 g/m$^2$/hr over a period of 72 hours.

However, as discussed above there are inherent risks and unwanted side effects associated with the administration of uridine. The administration of UDPG as a rescue agent overcomes the deficiencies of the prior art. The invention is illustrated as shown by the examples below.

Comparative Example 1—Establishing Toxic Levels of 5-FU

A first group of ten CD8FI female mice having an average tumor weight of 120 mg was treated by i.v. with saline once a week for three weeks; a second group of ten CD8FI female mice having an average tumor weight of 120 mg was treated by i.v. with a single bolus of 100 mg/kg of 5-fluorouracil once a week for three weeks; and a third group of ten female CD8FI female mice having an average tumor weight of 120 mg was treated by i.v. with a single bolus of 150 mg/kg of 5-fluorouracil once a week for three weeks. Observations were recorded 6 days after the last injection. The results are reported in Table 2 on the following page:

TABLE 2

Toxicity of 5-FU

| Treatment | Percent Body Weight Change | Mortality | Tumor Weight (mgs) |
| --- | --- | --- | --- |
| 1) Saline | +4 | 1/10 | 3181 |
| 2) $FU_{100}$ | −4 | 0/10 | 688 |
| 3) $FU_{150}$ | −24 | 8/10 | 433 |

Table 2 shows that a therapeutic effect is obtained with the weekly maximum tolerated dose (MTD) for mice of 100 mg/kg of 5-fluorouracil. The 100 mg/kg/week concentration is not a toxic dose. However, a very lethal dose (80% mortality) is established at 150 mg/kg/week.

Comparative Example 2

FIG. 1 establishes that 5-FU administered by i.v. in doses of 130 mg/kg/wk to mice is a toxic dose. Toxicity is determined by a change in body weight. Ten CD8FI female mice with breast tumors were treated with weekly doses of 5-fluorouracil in amounts of 130 mg/kg for three weeks. The percent of body weight change of the mice is shown and plotted over a period of approximately 12 days after administration of the last dose. The mice receiving 130 mg/kg of 5-FU suffered a weight loss of approximately 25% and a mortality of 30%. These results establish toxicity of fluorouracil in mice at 130 mg/kg/wk.

Example 1—Rescue Levels of UDPG

The experiment of the third group of mice of Comparative Example 1 ($5FU_{150}$), as reported in Table 2, was repeated except that after each injection of 5-FU, UDPG was administered orally by gavage in concentrations of 1500 mg/kg 2 hours after each weekly dose of 5-fluorouracil. Two and one-half hours later, after the first administration of UDPG, additional oral administrations of UDPG were made in concentrations of 2000 mg/kg every 8 hours 5 times. Ten mice were also treated orally by gavage with UDPG at concentrations of 1950 mg/kg 2 hours after each weekly administration of 5-fluorouracil. Subsequently, UDPG was orally administered 2½ hours later at concentrations of 2600 mg/kg every 8 hours 5 times. The results are shown in Table 3.

TABLE 3

5-FU and oral UDPG rescue

| Treatment | Percent Body Weight Change | Mortality | Tumor Weight (mgs) |
| --- | --- | --- | --- |
| 4) $5\text{-}FU_{150}$ and $UDPG_a$ | −20 | 2/10 | 431 |
| 5) $5\text{-}FU_{150}$ and $UDPG_b$ | −20 | 1/10 | 212 | a - 2 hrs after FU, UDPG at 1500 mg/kg, then 2.5 hrs 2000 mg/kg q. 8 hr × 5 b - 2 hrs after FU, UDPG at 1950 mg/kg, then 2.5 hrs 2600 mg/kg q. 8 hr × 5

As can be seen from the mortality data in Table 2 and Table 3 administering UDPG in concentrations as indicated reduces the toxicity of 5-fluorouracil—even when the dose of 5-FU is a lethal dose (if 5-FU was administered alone). The data thus establishes the rescue effect of orally administered UDPG. As shown in the "tumor weight" data, an enhanced therapeutic effect (tumor weight=212) is achieved as evidenced by the reduction in tumor weight relative to the control data presented in Table 2, where the tumor weight was 688 mg in the control group receiving the maximum tolerated dose of 100 mg/kg/wk of 5-FU alone.

Comparative Example 3—Confirmation of Uridine Rescue

The experiment of the third group of mice of Comparative Example 1 was repeated except that uridine was administered orally by gavage at 600 mg/kg 2 hours after the administration of 5-FU, and then 2½ hours later at a concentration of 800 mg/kg every 8 hr 5 times. A second trial was repeated by administering uridine 2 hours after the administration of 5-fluorouracil in a concentration of 780 mg/kg and then 2½ hours later at a concentration of 1,040 mg/kg every 8 hr×5. The results are reported in Table 4.

TABLE 4

5-FU and Oral Uridine Rescue

| Treatment | Percent Body Weight Change | Mortality | Tumor Weight (mgs) |
| --- | --- | --- | --- |
| 6) $5\text{-}FU_{150}$ and $UR_c$ | −23 | 4/10 | 242 |
| 7) $5\text{-}FU_{150}$ and $UR_d$ | −14 | 0/10 | 361 | c - 2 hrs. after FU, UR at 600 mg/kg, then 2.5 hrs, 800 mg/kg q. 8 hr × 5 d - 2 hrs. after FU, UR at 780 mg/kg, then 2.5 hrs 1,040 mg/kg q. 8 hr × 5

The data confirms the rescue effect of uridine for the two different schedules of administration and the therapeutic effect of 5-fluorouracil. That is, the mortality is decreased as compared to Group 3 of Example 1 and tumor weights are decreased relative to the control of Group 2 of Example 1 where the tumor weight is 688 mg after administrations of the MTD.

Comparative Example 4

It is known that BAU administered in vivo allows uridine to accumulate in the body, as BAU has been shown to prevent the breakdown of uridine by phosphorylase and the subsequent rapid body clearance of uridine. Accordingly, since it has been determined by the present results that UDPG provides a source of uridine, it is one extension of the present invention to include the administration of BAU when using UDPG as a rescue agent. BAU can be administered simultaneously, before or after the addition of UDPG.

The experiment of the third group of mice of Comparative Example 1 was repeated using 150 mg/kg of 5-fluorouracil. However, after each weekly injection of FU, BAU was administered orally by gavage at concentrations of 250 mg/kg 2 hours after the last administration of 5-fluorouracil and subsequent administrations of BAU were made 4½ hours after the administration of 5-fluorouracil and then every 8 hours four times.

The results are reported in Table 5

TABLE 5

5-FU and oral BAU

| Treatment | Percent Body Weight Change | Mortality | Tumor Weight (mgs) |
|---|---|---|---|
| FU$_{150}$ and BAU$_e$ | — | 10/10 | — | e - BAU at 250 mg/kg 2 hrs and then 4.5 hrs after FU and then q. 8 hr × 4

It is clear that 5-FU in concentrations of 150 mg/kg/wk is a lethal dose and the addition of BAU alone fails to provide a rescue effect. As confirmed in the examples below a rescue benefit does not occur without the presence of added UDPG or added uridine.

Example 2—Rescue Levels of Oral UDPG with Oral BAU

The experiment of Group 4 of Example 1 was repeated except that BAU was administered orally by gavage at a dosage of 250 mg/kg 2 hours after the administration of 5-FU, along with the first administration of UDPG. BAU was then administered orally by gavage 4½ hours after the administration of 5-fluorouracil and then every 8 hours four times. The results are reported in Table 6.

TABLE 6

5-FU and Oral UDPG and Oral BAU

| Treatment | Percent Body Weight Change | Mortality | Tumor Weight (mgs) |
|---|---|---|---|
| FU$_{150}$ and UDPG$_a$ + BAU$_e$ | −16 | 0/10 | 478 |
| FU$_{150}$ and UDPG$_b$ + BAU$_e$ | −11 | 0/10 | 431 | a - UDPG at 1500 mg/kg 2.5 hrs 2000 mg/kg q. 8 hr × 5
b - UDPG at 1950 mg/kg 2.5 hrs 2600 mg/kg q. 8 hr × 5
e - BAU at 250 mg/kg 2 hrs and 4.5 hrs after FU and then q. 8 hr × 4

Once again toxicity is shown to be reduced and a safe therapeutic effect is established that is greater than that achieved by FU alone at its MTD of 100 mg/kg.

Comparative Example 5—Confirmation of Oral Uridine Rescue with Oral BAU

Comparative Example 3 was repeated except BAU was administered at a dosage of 250 mg/kg 2 hours after the administration of 150 mg/kg of 5-FU along with the administration of uridine. BAU was then orally administered 4½ hours after the administration of 5-fluorouracil and then every 8 hours 4 times. The results are reported in Table 7.

TABLE 7

5-FU and Oral Uridine Rescue plus BAU

| Treatment | Percent Body Weight Change | Mortality | Tumor Weight (mgs) |
|---|---|---|---|
| FU$_{150}$ and UR$_c$ + BAU$_e$ | −13 | 0/10 | 475 |
| FU$_{150}$ and UR$_d$ + BAU$_e$ | −8 | 1/10 | 434 | c - 600 mg/kg 2.5 hrs, then 800 mg/kg q. 8 hr × 5
d - 780 mg/kg 2.5 hrs, then 1,040 mg/kg q. 8 hr × 5
e - BAU at 250 mg/kg 2 hrs and 4.5 hrs after FU and then q. 8 hr × 4

As shown in Table 7 the data confirms the effectiveness of uridine rescue and BAU administration. In comparing Tables 6 and 7 it is seen that the therapeutic and toxic effects of UDPG and BAU therapy are very similar to uridine and BAU therapy after the administration of 5-FU.

However, as discussed above, the dose of uridine required to obtain a rescue effect is limited by toxicity, i.e. by the onset of diarrhea, fever and/or phlebitis. The administration of UDPG, surprisingly and unexpectedly, does not cause fever and phlebitis when administered in a peripheral vein, and does not cause diarrhea even when taken orally in amounts of 2 grams. The result is surprising because UDPG does break down to provide pools of uridine. Parenteral results are set forth in Tables 8–10 below which show increased plasma levels of uridine after the administration of UDPG.

TABLE 8

(peripheral vein)
UDPG 2 g in 60 minutes plus UDPG 2 g in 20 minutes

| Time | Uridine plasma levels (μM/mol) |
|---|---|
| 0 | 0 |
| 15' | 136 |
| 30' | 148 |
| 60' (end 1st infusion) | 124 |
| 80' (end 2nd infusion) | 334 |
| 95' | 138 |
| 120' | 113 |
| 240' | 92 |

Table 8 shows plasma levels of uridine in human patients receiving a first i.v. dose of UDPG of 2 grams over a sixty minute period and thereafter a second i.v. 2 gram dose over a twenty minute period. As is seen plasma concentrations of uridine increase with administration of UDPG and fall when administration stops.

TABLE 9

(parenteral)
UDPG administered in 4 g over 30 minutes

| Time | Uridine plasma levels (μM/mol) |
|---|---|
| 0 | 0 |
| 15' | 353 |
| 30' | 865 |
| 60' | 175 |
| 120' | 115 |
| 240' | 75 |

Table 9 shows the uridine plasma levels in human patients receiving an i.v. dose of UDPG of 4 grams over a thirty minute period. Again plasma levels of uridine increase with administration and fall after administration.

TABLE 10

| | UDPG 6 g over 60 minutes |
|---|---|
| Time | Uridine plasma levels (μM/mol) |
| 0 | 0 |
| 15' | 180 |
| 30' | 300 |
| 60' | 935 |
| 120' | 215 |
| 240' | 81 |

Table 10 shows the uridine plasma levels in human patients receiving an i.v. dose of UDPG of 6 grams over a sixty minute period. The results obtained are similar to the results as reported above in Tables 8 and 9.

In administering UDPG by the parenteral route no fever and no phlebitis occurred at the site of peripheral injection (antecubital vein).

As shown in the examples above, UDPG is effective in providing rescue after the administration of antipyrimidine anti-cancer agents or related compounds.

5-fluorouracil is administered in amounts of at least 600 mg/m$^2$/wk in human patients as evidenced from Table 1 above. A proposed range for the administration of UDPG via i.v. is approximately 1–6 g/m$^2$/h over an interval of 1–3 hours with 2–3 hour intervals of rest up to 72 hours after the administration of 5-FU, i.e., in amounts of between 24 g/m$^2$/wk and 216 g/m$^2$/wk. The administration begins approximately 1–4 hours after the administration of 5-FU. If UDPG is to be administered orally then 2–8 g/m$^2$ of UDPG may be administered every 4–6 hours for 3 days starting 1–3 hours after the administration of 5-FU. In a limited human test UDPG has been taken orally in 4 gm doses without side effects and without toxicity. Based on this test it is expected that much higher amounts, for example 20 to even as high as 40 gm every 6 hours may be given per administration over a 72 hour period.

BAU may be administered orally at the rate of 0.5–2 g/m$^2$ every 4–6 hours for 3 days starting ½–2 hours after 5-FU administration, i.e., between 6 g/m$^2$/wk and 36 g/m$^2$/wk. Based on animal data BAU is non-toxic. Accordingly, it appears that the amounts of BAU which can be administered are not limited by toxic effects and, therefore, increased amounts of BAU may be administered.

Accordingly the proposed ratio of 5-fluorouracil/UDPG/BAU is 1:40 to 800:5 to 200 preferably 1:40 to 360:10 to 60.

Figure 2:
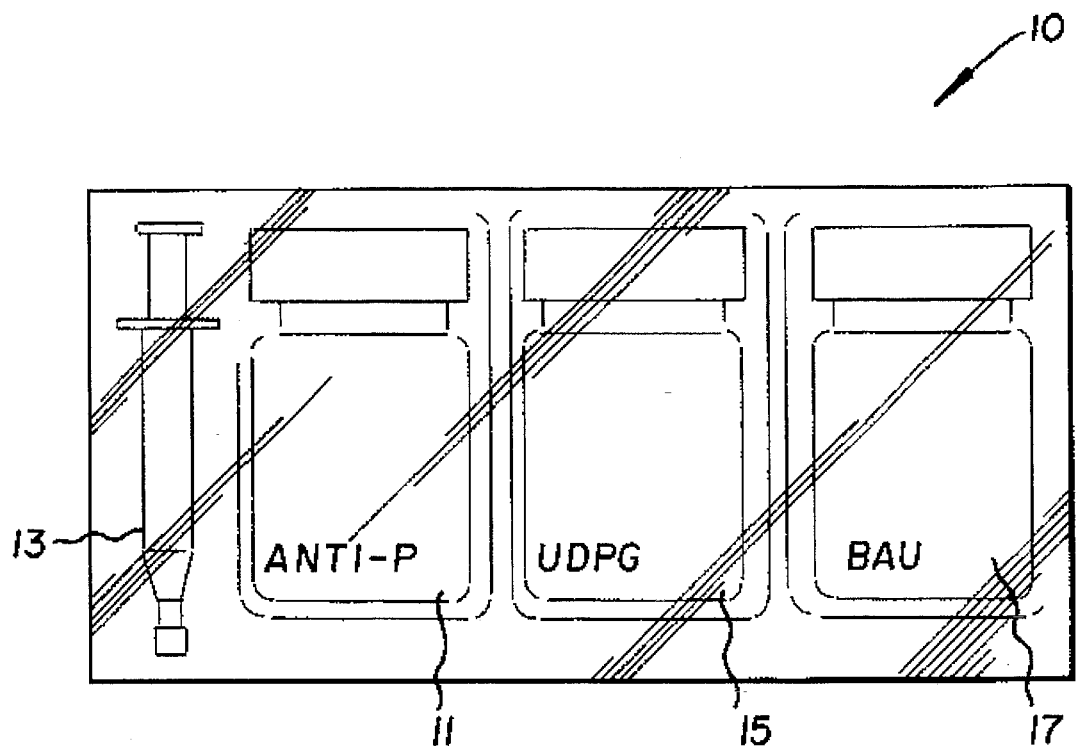
FIG. 2 is a schematic diagram of the kit of the present invention.

The components of the invention can be assembled into kits as shown in FIG. 2, with the kits containing unit dosages of the effective ingredients. Specifically, a kit 10 may include an effective dose of the pyrimidine inhibitor such as 5-fluorouracil in dosage ampule 11. Pyrimidine inhibitors are always administered parenterally and, therefore, the kit may also include a syringe 13. The kit will also contain an effective dose of the rescue agent UDPG. UDPG, as discussed above, is basically an antidote for the pyrimidine inhibitor and may be administered orally or parenteral. Accordingly, UDPG will be packaged separately from the pyrimidine inhibitor and may be packaged in a dosage ampule 15 for parenteral administration, or in a sachet for oral administration.

The kit may also contain an effective unit dose of the uridine phosphorylase inhibitor BAU. BAU is administered orally and, therefore, BAU may be packaged in the kit separately from the other ingredients in the form of a dosage ampule 17 or sachet.

It should be apparent that many modifications may be made to the invention without departing from the spirit and scope of the invention. That is, as discussed above, antipyrimidine therapy may be only one of many anti-cancer therapies being given to a cancer patient. Regardless of the number of therapies, so long as an antipyrimidine anti-tumor agent is administered, rescue with UDPG can be accomplished. Of course, if combination therapy is being given, doses of the antipyrimidine anticancer agent as reported herein may have to be reduced to avoid drug mortality. Therefore, FIGS. 1 and 2 and the examples of the application are only used for illustration and direction. The invention is limited only in scope by the appended claims.

What is claimed:

1. A method of rescuing tumor-bearing patients to whom an anti-tumor effective amount of a pyrimidine inhibitor has been administered, which comprises:

administering to the tumor bearing patient, after the administration of the anti-tumor pyrimidine inhibitor, a rescue effective amount of UDPG.

2. The method of claim 1 wherein UDPG is administered parenterally.

3. The method of claim 1 wherein UDPG is administered at least 1 hour after the administration of the anti-tumor pyrimidine inhibitor.

4. The method of claim 3, wherein said UDPG is administered orally.

5. The method of claim 1 wherein the pyrimidine inhibitor is F-dUMP or a metabolic precursor thereof.

6. The method of claim 5 wherein the metabolic precursor is 5-fluorouracil.

7. The method of claim 5, wherein said UDPG is administered orally.

8. The method of claim 1 wherein the anti-tumor effective amount of the pyrimidine inhibitor is a toxic amount absent the administration of a rescue effective amount of UDPG.

9. The method of claim 8, wherein said UDPG is administered orally.

10. The method of claim 1 wherein the anti-tumor effective amount of the pyrimidine inhibitor is an amount between greater than a maximum tolerated dose and a lethal dose absent the administration of a rescue effective amount of UDPG.

11. The method of claim 10, wherein said UDPG is administered orally.

12. The method of claim 1, wherein UDPG is administered up to 3 hours after the administration of the antipyrimidine agent.

13. The method of claim 1, wherein said UDPG is administered orally.

14. A method of treating a tumor in a patient, said method comprising:

administering an anti-tumor effective amount of an antipyrimidine agent to the patient; and administering a rescue effective amount of UDPG after administration of the antipyrimidine agent.

15. The method of claim 14 wherein the antipyrimidine agent is F-dUMP or a metabolic precursor thereof, 16. The method of claim 15 wherein the anti-tumor effective amount of the antipyrimidine agent is an amount between greater than a maximum tolerated dose and a lethal dose absent the administration of a rescue effective amount of UDPG.

17. The method of claim 15 wherein the anti-tumor effective amount of the pyrimidine inhibitor is a toxic amount absent the administration of a rescue effective amount of UDPG.

18. The method of claim 14, wherein said UDPG is administered orally.

19. The method of claim 14, wherein said UDPG is administered up to three hours after the administration of the anti-pyrimidine agent.

20. In a method for treating a tumor in a patient with an anti-tumor effective amount of an antipyrimidine agent, the improvement comprising administering rescue effective amounts of UDPG after administration of the antipyrimidine agent.

21. An anti-tumor kit, comprising:
   (A) an anti-tumor effective amount of a pyrimidine inhibitor, and
   (B) a rescue effective amount which is at least 2 grams of UDPG;

wherein (A) and (B) are separately packaged in said kit.

22. The kit of claim 21 wherein the anti-tumor pyrimidine inhibitor is F-dUMP or a metabolic precursor thereof.

23. The kit of claim 22 wherein the metabolic precursor is 5-fluorouracil.

24. The kit of claim 21 wherein the rescue effective amount of UDPG is present in a sachet for oral administration.

* * * * *